United States Patent [19]

Sarver et al.

[11] Patent Number: 5,376,120
[45] Date of Patent: Dec. 27, 1994

[54] BIOCOMPATIBLE IMPLANT AND METHOD OF USING SAME

[75] Inventors: David R. Sarver, Logansport; Roy C. Wiley, Warsaw, both of Ind.

[73] Assignee: Biomet, Inc., Warsaw, Ind.

[21] Appl. No.: 964,197

[22] Filed: Oct. 21, 1992

[51] Int. Cl.$^5$ .......................... A61F 2/28; A61F 2/02; A61F 2/54

[52] U.S. Cl. ........................ 623/16; 623/11; 623/66

[58] Field of Search ................ 623/11, 16, 66

[56] References Cited

U.S. PATENT DOCUMENTS

| | | | |
|---|---|---|---|
| Re. 32,026 | 11/1985 | Yamashita et al. | 126/263 |
| 3,585,982 | 6/1971 | Hollinshead et al. | 126/263 |
| 3,804,077 | 4/1974 | Williams | 126/263 |
| 3,889,483 | 6/1975 | Donnelly | 62/4 |
| 3,906,926 | 9/1975 | Staples | 126/263 |
| 3,980,070 | 9/1976 | Krupa | 126/263 |
| 4,057,047 | 11/1977 | Gossett | 126/263 |
| 4,077,390 | 3/1978 | Stanley et al. | 126/263 |
| 4,093,424 | 6/1978 | Yoshida et al. | 44/3 C |
| 4,106,478 | 8/1978 | Higashijima | 126/263 |
| 4,114,591 | 9/1978 | Nakagawa | 126/263 |
| 4,211,325 | 7/1980 | Wright | 206/438 |
| 4,245,359 | 1/1981 | Stuhmer | 3/1.9 |
| 4,279,249 | 7/1981 | Vert et al. | 128/92 D |
| 4,282,005 | 8/1981 | Sato et al. | 44/3 R |
| 4,293,962 | 10/1981 | Fuson | 3/1.9 |
| 4,302,855 | 12/1981 | Swanson | 3/1.9 |
| 4,337,773 | 7/1982 | Raftopoulos et al. | 128/305 |
| 4,344,190 | 8/1982 | Lee et al. | 3/1.9 |
| 4,379,448 | 4/1983 | Kapralis et al. | 126/263 |
| 4,516,564 | 5/1985 | Koiso et al. | 126/263 |
| 4,522,190 | 6/1985 | Kuhn et al. | 126/263 |
| 4,572,158 | 2/1986 | Fiedler | 126/263 |
| 4,671,410 | 6/1987 | Hansson et al. | 206/438 |
| 4,686,973 | 8/1987 | Frisch | 128/924 Z |
| 4,712,681 | 12/1987 | Branemark et al. | 206/478 |
| 4,743,257 | 5/1988 | Tormala et al. | 623/16 |
| 4,750,619 | 6/1988 | Cohen et al. | 206/438 |
| 4,872,442 | 10/1989 | Manker | 126/263 |
| 4,880,953 | 11/1953 | Manker | 219/10.55 M |
| 4,891,263 | 1/1990 | Kotliar | 428/225 |
| 4,916,193 | 4/1990 | Tang et al. | 525/413 |
| 4,920,203 | 4/1990 | Tang et al. | 524/409 |
| 4,923,470 | 5/1990 | Dumican | 623/11 |
| 4,950,295 | 8/1990 | Weigum et al. | 623/16 |
| 4,997,448 | 3/1991 | Filer | 623/23 |
| 5,009,666 | 4/1991 | Van Syckle et al. | 623/23 |
| 5,035,230 | 7/1991 | Steidl et al. | 126/263 |
| 5,037,442 | 8/1991 | Wintermantel et al. | 623/16 X |
| 5,046,479 | 9/1991 | Usui | 126/204 |
| 5,061,287 | 10/1991 | Feiler | 623/16 |
| 5,080,665 | 1/1992 | Jarrett et al. | 606/219 |
| 5,092,891 | 3/1992 | Kummer et al. | 623/16 |
| 5,117,809 | 6/1992 | Scaringe et al. | 126/263 |

FOREIGN PATENT DOCUMENTS 0086880  8/1983  European Pat. Off. ............. 623/16
0185453A2  6/1986  European Pat. Off. .

OTHER PUBLICATIONS

Barrows, T. H., "Degradable implant materials: a review of synthetic absorbable polymers and their applications," Clinical Materials, 1986, 1, pp. 233–257.

Primary Examiner—Randall L. Green
Assistant Examiner—Dinh X. Nguyen
Attorney, Agent, or Firm—Harness, Dickey & Pierce

[57] ABSTRACT

A biocompatible implant for forming a barrier within a cavity formed in living tissue, the living tissue being at a first thermochemical state. The biocompatible implant includes a main body which is able to be inserted into the cavity. The biocompatible implant further includes a flange for securing the main body in a substantially stationary position within the cavity. The flange is relatively rigid at the first thermochemical state but is relatively deformable at a second thermochemical state.

27 Claims, 5 Drawing Sheets

BIOCOMPATIBLE IMPLANT AND METHOD OF USING SAME

BACKGROUND OF THE INVENTION

This invention relates generally to medical implant devices, and more particularly to a biocompatible implant that is deformable at elevated temperatures and relatively rigid at body temperature.

A natural joint in the human body such as a hip joint may undergo degenerative changes due to a variety of etiologies. When these degenerative changes become advanced and are irreversible, it may ultimately become necessary to replace the natural joint with a prosthetic joint. Such a prosthetic joint is often formed from a high strength material that is not only able to accommodate the various loading conditions that the artificial joint may encounter, but is also biocompatible with the human body. Examples of such high strength materials used for the manufacture of prosthetic joints include metal alloys such as titanium or cobalt chrome alloys, metal alloys having metallic porous coatings secured to the outside thereof, and composite materials.

The general procedure that is used to replace certain natural joints with prosthetic joints will now be described with specific reference to a hip joint replacement. When implantation of a hip joint prosthesis becomes necessary, the head of the natural femur is resected. The acetabulum is then reamed so as to receive the acetabular component of the hip joint prosthesis. After the acetabular component has been implanted in the acetabulum, the intramedullary canal of the femur that is used for receiving and supporting the stem portion of the prosthetic hip is then reamed and/or rasped to form a cavity. A suitable adhesive such as bone cement is then introduced into the cavity. The stem portion of the prosthetic hip is then inserted into the cavity formed in the intramedullary canal, so that the stem portion becomes secured to the bone surrounding the cavity by the bone cement. A proper bonding of the external surface of the stem portion of the prosthetic hip to the wall of the cavity formed in the intramedullary canal requires that the bone cement be pressurized. This pressurization allows the bone cement to interdigitate with the wall of the intramedullary canal, as well as the external surface geometry of the stem portion of the prosthetic hip.

Under certain circumstances, it is desirable to limit or restrict the flow of bone cement from the area of the cavity immediately adjacent to the stem portion of the prosthetic hip into the lower portion of the cavity that is below the stem portion. Various methods have been used to restrict the flow of bone cement into the lower portion of the cavity. For example, fragments of biocompatible material such as hardened cement or bone have been inserted into the cavity which would then restrict the flow of bone cement into the lower portion of the cavity. In addition, permanent polyethylene plugs placed within the cavity have also been used to restrict the flow of bone cement into the lower portion of the cavity.

While these methods for restricting the flow of bone cement into the lower portion of the cavity have been successful, there are nevertheless various aspects of these methods that could be improved. For example, it is often difficult to remove hardened cement or bone fragments from the cavity, which is often necessary when the joint prosthesis is to be replaced by another prosthesis. In addition, polyethylene plugs are relatively rigid and therefore often tend to be relatively difficult to deform to the desired shape for easy placement within the cavity of the intramedullary canal. While the structural geometry of polyethylene plugs can be changed to improve the ease with which the plug can be inserted, such a plug may have a tendency to slide within the cavity when the cavity is pressurized so as to decrease the ability of the plug to maintain pressure.

The use of bone plugs made from bioresorbable materials has also been described in literature and have the advantage of being absorbed by the body over a period of time so as to allow for bone or fibrous material to grow into the space previously occupied by a bioresorbable plug. Such bioresorbable plugs are described as being made from a polymer such as polylactic acid. While these bioresorbable plugs may be capable of limiting the flow of bone cement into the lower portion of the cavity, they are presumably relatively rigid which would limit their ability to be easily manipulated into the desired location within the cavity unless they are made in a variety of sizes.

A need therefore exists for a bioresorbable implant that restricts the flow of bone cement into the lower pollution of a cavity formed in the intramedullary canal when the bone cement is pressurized, yet is sufficiently deformable so as to allow the bioresorbable implant to be positioned and manipulated into the proper location within the cavity with relative ease without the need for a relatively large number of sizes.

SUMMARY OF THE INVENTION

An advantage of the present invention is to provide a biocompatible implant that is relatively rigid at a first thermochemical state after implantation within a living body and relatively deformable at a second thermochemical state to which the implant is temporarily brought prior to implantation. Another advantage of the present invention is to provide a biocompatible implant which is relatively rigid at body temperature and relatively deformable at another temperature.

A further advantage of the present invention is to provide a bone plug that is able to restrict the flow of bone cement in a cavity formed in the intramedullary canal from a region laterally adjacent to a prosthetic implant to a position below the prosthetic implant. A related advantage of the present invention is to provide a bone plug that is both resorbable and deformable.

Another advantage of the present invention is to provide a bioresorbable implant that is relatively easy to insert into a cavity formed within living tissue yet is able to be relatively rigidly secured to the tissue.

A further advantage of the present invention is to provide a biocompatible implant that is deformable when the implant is being inserted into a cavity formed within human tissue but becomes relatively rigid once the biocompatible implant is located in its final position.

The present invention, in one form thereof, provides a biocompatible implant for forming an enclosed pressure region within a cavity formed in living tissue. The biocompatible implant includes a main body which is operable to be inserted into the cavity. The biocompatible implant further includes means for securing the main body in a substantially stationary position within the cavity. The means for securing the main body is relatively rigid at a first temperature and is deformable at a second temperature that is above the first temperature.

More specifically, the biocompatible implant of the present invention comprises a substantially cylindrical main body having one or more planar flanges extending outwardly therefrom. Each flange includes a plurality of ridges on one surface which contact the wall of the cavity formed in the intramedullary canal upon insertion. The flanges serve to maintain the biocompatible implant in a substantially stationary position within the cavity formed within the intramedullary canal. In addition, the flanges restrict the flow of bone cement in the cavity away from a position well below the implant prosthesis.

The invention, in another form thereof, provides a method for implanting a biocompatible implant into human tissue that includes the steps of heating the implant to a temperature substantially that of its glass transition temperature to allow the biocompatible implant to be deformed. The biocompatible implant is then inserted into a cavity formed within the tissue to a preselected position. The biocompatible implant is then allowed to cool to a temperature where it becomes relatively rigid.

BRIEF DESCRIPTION OF THE DRAWINGS

Other advantages of the present invention will become apparent to one skilled in the art upon reading the following specification and the following drawings.

DETAILED DESCRIPTION OF THE PREFERRED EMBODIMENT

It should be understood that while this invention is described in connection with a particular example, the scope of the invention need not be so limited. Rather, those skilled in the art will appreciate that the following teachings can be used in a much wider variety of applications than the examples specifically mentioned herein.

Figure 1:
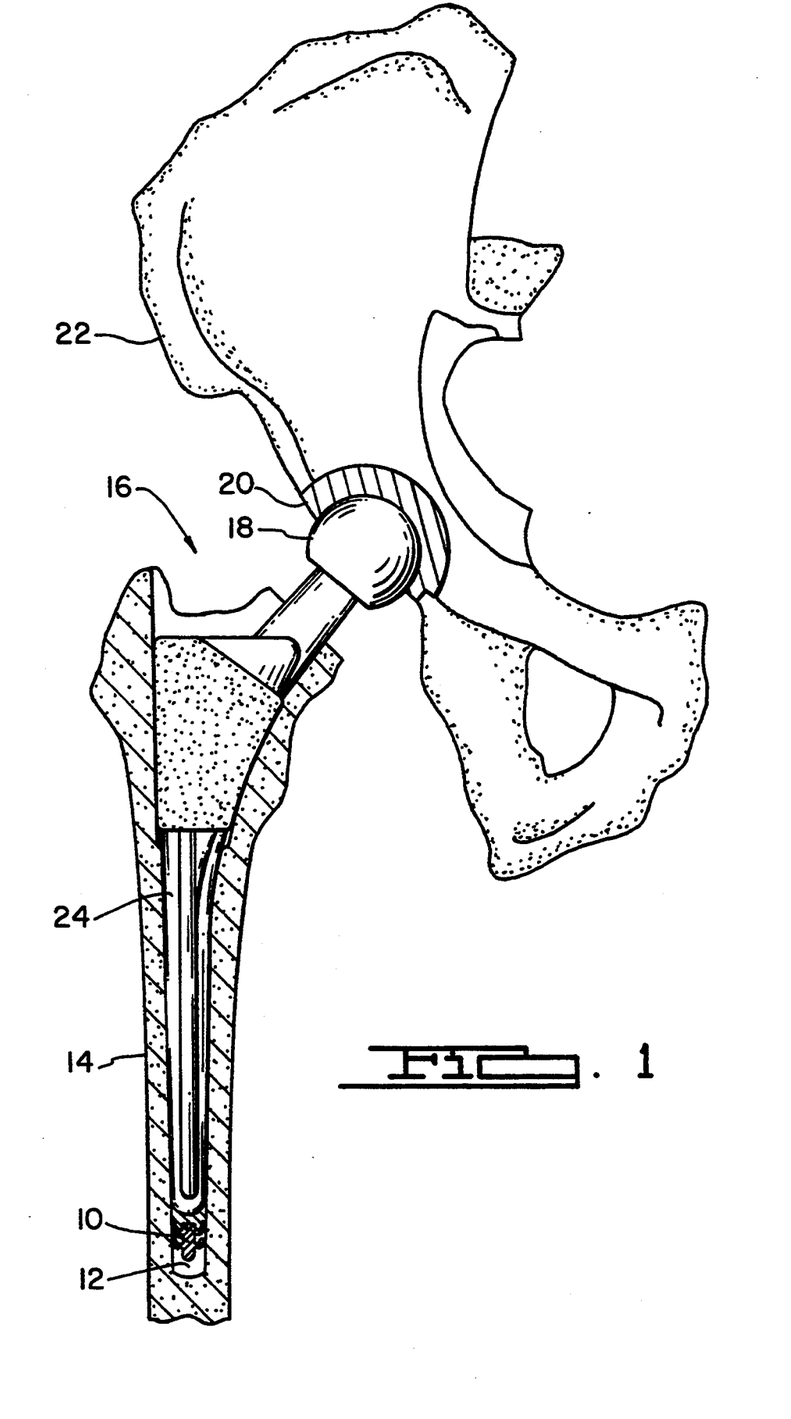
FIG. 1 is a cross-sectional view of a biocompatible implant according to the teachings of the preferred embodiment of the present invention shown in association with a hip joint prosthesis.

Referring now to FIG. 1, there is shown a biocompatible implant 10 according to the preferred embodiments of the present invention. The biocompatible implant 10 is shown as being disposed within a cavity 12 formed in the intramedullary canal of a femur 14. A hip joint prosthesis, generally designated by the numeral 16, is positioned within the cavity 12. The hip joint prosthesis 16 is shown to include a head component 18 for engaging an acetabular component 20 that is secured to the pelvis 22. The hip joint prosthesis 16 further includes a stem portion 24 that is inserted into the cavity 12 and that is used to secure the hip joint prosthesis 16 to the femur 14. As seen in FIG. 1, the biocompatible implant 10 is positioned within the cavity 12 beyond the distal end of the stem portion 24 of the hip joint prosthesis 16.

While the biocompatible implant 10 is depicted as being a bone plug, it will be appreciated that the biocompatible implant 10 may be any other type of biocompatible or bioresorbable implant exhibiting similar properties that is also deformable at a thermochemical state different from that existing within a body but is relatively rigid at a thermochemical state existing within a body. A "thermochemical state" as used in describing the present invention is defined as a combination of thermal and chemical conditions resulting from exposure to certain thermal and chemical environments. Although one type of change in thermochemical state occurs by a change of temperature alone, changes in thermochemical state of a biocompatible implant of the present invention should be understood as not limited only to changes in temperature.

Figure 2:
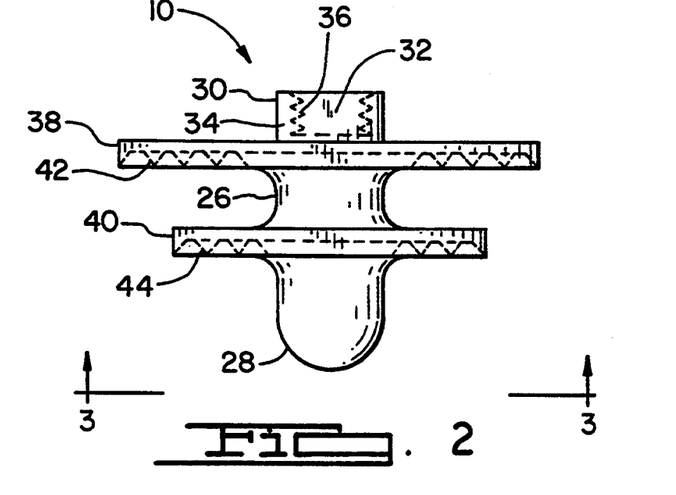
FIG. 2 is an enlarged elevational view of a biocompatible implant shown in FIG. 2 according to the teachings of the preferred embodiment of the present invention.

Referring now to FIG. 2, the biocompatible implant 10 includes a main body 26 having a rounded lower end 28 and an upper end 30. The upper end 30 includes an open recess 32 that is defined by an annular wall 34 and is used to receive an insertion tool (not shown). The annular wall 34 is shown to include a plurality of threads 36 that are disposed on the inner surface of the annular wall 34. The threads 36 are sized to receive a matching threaded end of the insertion tool that allows the biocompatible implant 10 to be removably secured to the insertion tool. It will be appreciated, however, that any other suitable means for allowing the biocompatible implant 10 to be inserted into the cavity 12 by an insertion tool may be used.

To provide means for securing the main body 26 in a substantially stationary position within the cavity 12, the biocompatible implant 10 further includes an upper first flange 38 and a lower second flange 40 that extend radially from the main body 26. Both the first and second flanges 38 and 40 are planar and circular in nature, with the diameter of the first flange 38 being larger than the diameter of the second flange 40. The first and second flanges 38 and 40 are used for engaging the wall of the cavity 12 when biocompatible implant 10 is inserted into the cavity 12. In addition, the flanges 38 and 40 also enhance a seal for restricting the flow of bone cement from the portion of the cavity 12 above the biocompatible implant 10 to the portion of the cavity 12 directly below the biocompatible implant 10. While the biocompatible implant 10 has been shown to include the first and second flanges 38 and 40, other suitable means for securing the biocompatible implant 10 within the cavity 12 may be used.

Figure 3:
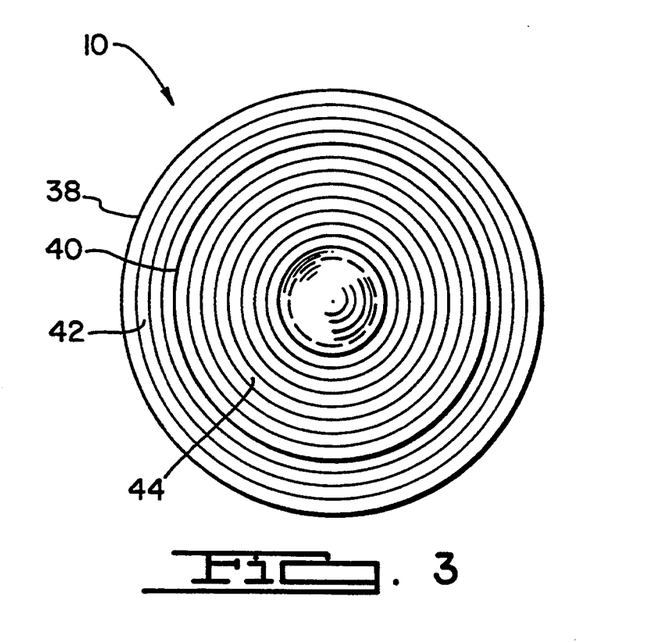
FIG. 3 is a view of a biocompatible implant accordance with a preferred embodiment of the present invention taken in the direction of line 3—3 in FIG. 2.

The first flange 38 includes a plurality of concentric ridges 42 disposed on its lower surface while the second flange 40 also has a plurality of concentric ridges 44 disposed on its lower surface as shown in FIG. 3. The ridges 42 and 44 serve to enhance the positional stability of the biocompatible implant 10 within the cavity 12 by engaging the walls of the cavity 12 upon insertion therein of the biocompatible implant 10.

In a preferred embodiment, the biocompatible implant 10 is formed from a bioresorbable material that is substantially rigid at body temperature but becomes pliable or deformable at temperature somewhat above body temperature. One such material is an 82:18 copolymer of polylactic acid and polyglycolic acid. The glass transition temperature of this material is between approximately 40° C. and 60° C. so that heating of the biocompatible implant 10 to a deformable temperature preferably 5°–10° above the glass transition temperature allows the biocompatible implant 10 to be easily deformed as the biocompatible implant 10 is inserted into the cavity 12 in the manner described below. It should be understood that other suitable biocompatible materials may be used that have a glass transition temperature above body temperature. These materials include polymers, copolymers, fibers and films of polyglycolide, polylactide, polydioxanone, poly(glycolide-co-trimethylene carbonate), poly(ethylene carbonate), poly(iminocarbonates), polycaprolactone, polyhydroxybutyrate, polyesters, poly(amino acids), poly(esteramides), poly(orthoesters), poly(anhydrides) and cyanoacrylates and copolymers and blends thereof. A review of these materials as well known degradable synthetic implant materials is set forth in Barrows, T.H., *Degradable Implant Materials: A Review of Synthetic Absorbable Polymers and their Applications,* Clinical Materials 1986: 1: 233–257, which is hereby incorporated by reference.

Figure 4:
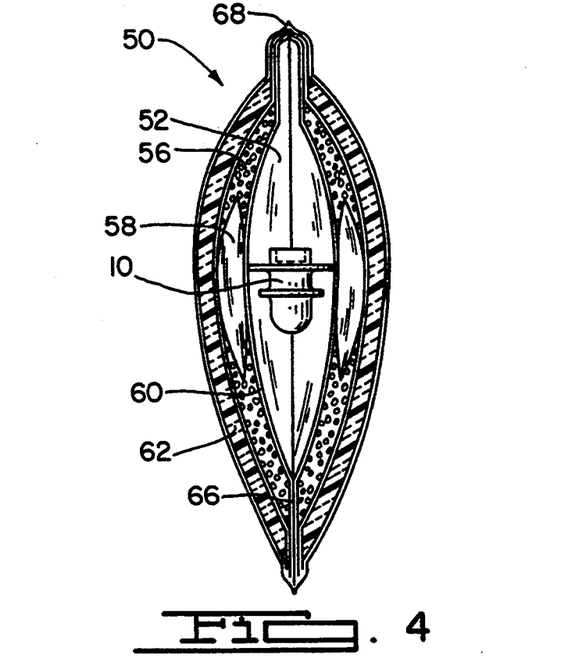
FIG. 4 is a cross-sectional view of a thermal packaging unit used for heating the biocompatible implant shown in FIG. 2 according to the teaching of a preferred embodiment of the present invention.

As shown in FIG. 4, the biocompatible implant 10 may be heated by a thermal packaging unit 50. As will be more fully discussed below, the thermal packaging unit 50 is able to generate thermal energy that is transferred to the biocompatible implant 10 so as to cause the temperature of the biocompatible implant 10 to be substantially that of its glass transition temperature. Because the biocompatible implant 10 is deformable at this elevated temperature, the biocompatible implant 10 may be relatively easily inserted into the cavity 12 of the femur 14. It will also be noted from the following discussion that the thermal packaging unit 50 is self-contained in that the elements used for heating the biocompatible device 10 are located within the thermal packaging unit 50.

To provide means for heating the biocompatible implant 10, thermal packaging unit 50 includes a first compartment 56 that defines a storage area 52 for receiving the biocompatible implant 10, and a second compartment 58 that is disposed within the first compartment 56. The first compartment 56 includes an inner wall 60 that is disposed adjacent to the storage area 52 and an external surface defined by an outer wall 62. The inner wall 60 and outer wall 62 act as a barrier to moisture, microbes or other contaminants which enhances a relatively sterile and relatively dry condition within the storage area 52 thereby minimizing degradation of the biocompatible implant 10 by exposure to the environment.

The inner wall 60 is preferably made from a laminate including a linear low density film of 3 to 4 mils thickness, a high temperature adhesive layer, an aluminum foil layer, a second high temperature adhesive layer and a second linear low density film of 3 to 4 mils thickness, although other suitable materials may be used. The outer wall 62 is preferably made from a laminate including a linear low density film of 3 to 4 mils thickness, a high temperature adhesive layer, an aluminum foil layer, a second high temperature adhesive layer and an insulating layer, although other suitable materials may be used. The insulating layer may be made from any flexible insulating material well known to those skilled in the art and is used to retain the thermal energy generated within the first compartment 56. In one preferred embodiment, the insulating layer is a laminate including a 60 to 100 gauge biaxial oriented nylon sheet, a high temperature adhesive layer, a microfoam-blown polypropylene layer and a non-woven film, such as nylon. It will also be noted that the first compartment 56 may be separated into segments by means of a separating wall 66. The separating wall 66 can also be constructed to provide two second compartments 58 within thermal packaging unit 50 thereby making each half of thermal packaging unit 50 independently activated.

The thermal packaging unit 50 also includes a top seal 68 that maintains a relatively moisture-free environment within the storage area 52. The top seal 68 is preferably resealable so as to allow the biocompatible implant 10 to be reinserted into the storage area 52. This may be necessary when the temperature of the biocompatible implant 10 cools to a temperature below its glass transition temperature before the insertion process can be attempted or successfully completed.

The first compartment 56 is operable to contain calcium chloride while the second compartment 58 is operable to contain water. As will be appreciated by those skilled in the art, when the wall of second compartment 58 is ruptured, water from the second compartment 58 is able to combine with the calcium chloride in the first compartment 56 in an exothermic reaction. As this exothermic reaction occurs, thermal energy is transferred from the first compartment 56 to the biocompatible implant 10 which causes the temperature of the biocompatible implant 10 to rise. As the temperature of the biocompatible implant 10 reaches a temperature substantially that of its glass transition temperature, the biocompatible implant 10 becomes increasingly deformable and may be easily inserted into the cavity 12. After the biocompatible implant 10 has been inserted into the cavity 12, the biocompatible implant 10 cools to body temperature which is below the glass transition temperature of the biocompatible implant 10. When this occurs, the bioresorbable implant 10 becomes relatively rigid so as to resist further movement within the cavity 12.

The use of thermal packaging unit 50 will now be described in greater detail. Shortly before the biocompatible implant 10 is to be implanted, an insertion tool (not shown) is removably attached to the biocompatible implant 10 by threading the insertion tool onto the plurality of threads 36 that are disposed on the inner surface of the annular wall 34. The biocompatible implant 10 and the attached end of the insertion tool are then inserted into the thermal packaging unit 50. To enhance the heating operation, the top seal 68 is substantially closed around the insertion tool, which protrudes from the thermal packaging unit 50. Activation of thermal packaging unit 50 is then accomplished by gently squeezing thermal packaging unit 50 from its exterior so as to rupture second compartment 58. Rupturing the second compartment 58 allows water to escape from the second compartment 58 and contact the calcium chloride located within first compartment 56. The resulting exothermic reaction between the water and calcium chloride is able to heat the biocompatible implant 10 within the storage area 52 to a temperature of approximately 50° C. to 70° C. within approximately 2 minutes following activation. At this elevated temperature, the temperature of the biocompatible implant 10 is substantially that of its glass transition temperature and is therefore relatively deformable. With proper maintenance of top seal 68 in a substantially closed position, the thermal packaging unit 50 is capable of maintaining this elevated temperature of the storage area 52 for approximately 15–20 minutes so as to allow the biocompatible implant 10 to be reheated if necessary.

After the biocompatible implant 10 is heated to a temperature substantially that of its glass transition temperature, the top seal 68 of the thermal packaging unit 50 is opened from around the insertion tool and the biocompatible implant 10 and the insertion tool are removed from the thermal packaging unit 50 and are inserted, with the rounded lower end 28 of the biocompatible implant 10 first, into the cavity 12. As the biocompatible implant 10 enters the cavity 12, the first and second flanges 38 and 40 deform in a direction toward the open recess 32. Using the insertion tool, the biocompatible implant 10 is forced into the cavity 12 to a position approximately 1 to 2 centimeters past the expected position of the distal end of the stem 24 of the hip joint prosthesis 16. It should also be noted that it is possible to reinsert the biocompatible implant 10 into the thermal packaging unit 50 for reheating should a delay occur before the biocompatible implant 10 can be inserted into the cavity 12.

In approximately 1 to 2 minutes following removal of the biocompatible implant 10 from thermal packaging unit 50 and insertion into the cavity 12, the biocompatible implant 10 cools to a temperature below its glass transition temperature thereby returning to a relatively rigid condition. In this relatively rigid condition, the biocompatible implant 10 is secured in a substantially stationary position within cavity 12. After the biocompatible implant 10 is secured in this manner, the insertion tool is detached from the biocompatible implant 10 and is removed from the cavity 12.

It should be noted that alternatively, the biocompatible implant 10 may be placed within the thermal packaging unit 50 without being attached to the insertion tool. In this embodiment, the top seal 68 can be substantially closed during the heating operation, and the insertion tool is attached to the biocompatible implant 10 immediately prior to the removal of the biocompatible implant 10 from the thermal packaging unit 50.

Figure 5:
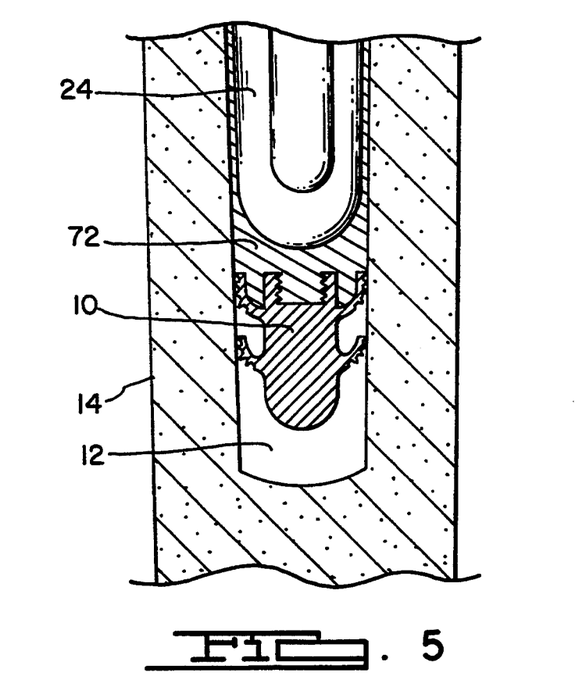
FIG. 5 is an enlarged cross-sectional view of a bioresorbable implant according to the teachings of the preferred embodiment of the present invention shown as being disposed within a cavity formed within the intramedullary canal of a femur.

After the biocompatible implant 10 is properly secured within the cavity 12 and has cooled below its glass transition temperature, bone cement 72 is introduced into the cavity 12 and the stem portion 24 is thereafter inserted into the cavity 12. The action of inserting the stem portion 24 into the cavity 12 causes pressurization of the bone cement 72 within the cavity 12 which causes the bone cement 72 to interdigitate with the stem portion 24 and the wall of the cavity 12. The first and second flanges 38 and 40 of the biocompatible implant 10 restrict the flow of the bone cement 72 to a position below the biocompatible implant 10 within the cavity 12. After the bone cement 72 is then given approximately 5 minutes to set, the stem portion 24 becomes secured to the femur 14. The final position of biocompatible implant 10, the bone cement 72 and stem portion 24 within the cavity 12 of femur 14 is illustrated in FIG. 5.

In a preferred embodiment, the biocompatible implant 10 is absorbed by natural functions within 1 to 1½ years. During and after this time, bone cells or a fibrous tissue may fill into the space previously occupied by the biocompatible implant 10 and the portion of the cavity 12 below the biocompatible implant 10.

As will be appreciated by those skilled in the art, the thermal packaging unit 50 may contain only one rupturable compartment whose contents may be introduced to air, water or an external activating compound in order to activate the exothermic or thermodynamic reaction which heats the biocompatible implant 10. In addition, three or more compartments may be used that can include different reactants that may be located within the first compartment 56. In this case, simultaneous exothermic reactions can occur by simultaneous rupturing of all barriers separating the compartments. Alternatively, the first compartment 56 may have multiple storage compartments for multiple supplies of the same chemical reactants. Such an arrangement would make it possible for sequential rupturing of these compartments so as to allow the duration of the thermal energy generated by the thermal packaging unit 50 to increase. Finally, the thermal packaging unit 50 may take the form shown in FIGS. 6–9. In these alternative embodiments, similar features common to those shown in FIG. 4 are referenced by numerals that are 100, 200 and 300 greater than the corresponding numerals in FIG. 4. Each of these alternative embodiments of the thermal packaging unit 50 will be more fully described below.

Figure 6:
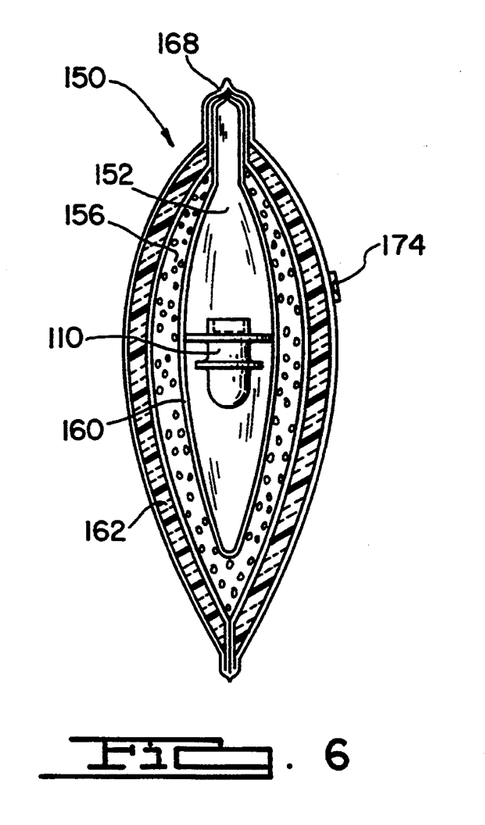
FIG. 6 is a cross-sectional view of a thermal packaging unit used for heating the biocompatible implant shown in FIG. 2 according to the teaching of another preferred embodiment of the present invention.

The thermal packaging unit 150 shown in FIG. 6 includes a first compartment 156 that defines a storage area 152 for receiving the biocompatible implant 10. The first compartment 156 includes an inner wall 160 that is disposed adjacent to the storage area 152 and an external surface defined by an outer wall 162. The inner wall 160 and outer wall 162 act as a microbial and moisture barrier which maintains a relatively sterile and relatively dry condition within the storage area 152 thereby minimizing degradation of the biocompatible implant 110 by exposure to the environment.

The inner wall 160 is preferably made from a laminate including a linear low density film of 3 to 4 mils thickness, a high temperature adhesive layer, an aluminum foil layer, a second high temperature adhesive layer and a second linear low density film of 3 to 4 mils thickness, although other suitable materials may be used. The outer wall 162 is made in a preferred embodiment from a laminate including a linear low density film of 3 to 4 mils thickness, a high temperature adhesive layer, an aluminum foil layer, a second high temperature adhesive layer and an insulating layer, although other suitable materials may be used. The insulating layer may be made from any flexible insulating material well known to those skilled in the art and is used to retain the thermal energy generated within the first compartment 156. In one preferred embodiment, the insulating layer is a laminate including a 60 to 100 gauge biaxial oriented nylon sheet, a high temperature adhesive layer, a microfoam-blown polypropylene layer and a non-woven film, such as nylon.

The thermal packaging unit 150 also includes a top seal 168 that maintains a relatively moisture-free environment within the storage area 152. The top seal 168 is preferably resealable so as to allow the biocompatible implant 110 to be reinserted into the storage area 152. This may be necessary when the temperature of the biocompatible implant 110 cools to a temperature below its glass transition temperature before the insertion process can be attempted or successfully completed.

Located on the exterior surface of the insulating layer 164 is an injection port 174 which is used to provide a resealable passageway from the external surface of the thermal packaging unit 150 to the first compartment 156. The injection port 174 is made from a compliant material that can be deformed and penetrated from an initial relatively sealed condition by an injection instrument such as a syringe or other suitable tool (not shown). It is preferred that the injection port 174 be located exterior to the outer wall 162 so as not to disturb the initial interior microbial and moisture conditions within the storage area 152. The injection port 174 preferably returns to a relatively sealed condition following the withdrawal of the injection instrument from the injection port 174.

The first compartment 156 is operable to contain calcium chloride which is reacted with water introduced by an injection instrument through the injection port 174. As water combines with the calcium chloride in the first compartment 156, an exothermic or thermodynamic chemical reaction occurs whereby thermal energy is generated within the first compartment 156 and is subsequently transferred from the first compartment 156 to the biocompatible implant 110 which causes the temperature of the biocompatible implant 110 to rise. It will be noted that the first compartment 156 may contain a different chemical reactant which may be combined with water or a suitable activating solvent other than water in the same manner described above to produce the desired exothermic or thermodynamic chemical reaction. It will also be noted that the first compartment 156 may be separated into segments by means of a separating wall, with a second injection port added for making each half of thermal packaging unit 150 independently activated.

Figure 7:
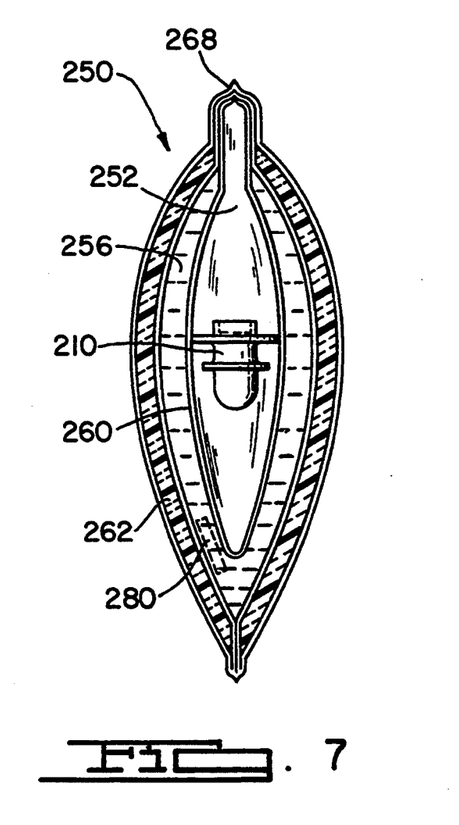
FIG. 7 is a cross-sectional view of a thermal packaging unit used for heating the biocompatible implant shown in FIG. 2 according to the teaching of yet another preferred embodiment of the present invention.

Another embodiment of the thermal packaging unit, generally designated by the numeral 250, is shown in FIG. 7. In this embodiment, the thermal packaging unit 250 includes a first compartment 256 that defines a storage area 252 for receiving the biocompatible implant. The first compartment 256 is operable to contain a supercooled solution of sodium acetate and water. Disposed within the solution is a metal activation disk 280, which is operable to crystallize the solution of sodium acetate and water upon bending. The activation disk 280 is available from Prism Technologies and is operable to crystallize the sodium acetate and water solution in a manner described below. The first compartment 256 includes an inner wall 260 that is disposed adjacent to the storage area 252 and an external surface defined by an outer wall 262. The inner wall 260 and outer wall 262 act as a microbial and moisture barrier which maintains a relatively sterile and relatively dry condition within the storage area 252 thereby minimizing degradation of the biocompatible implant 210 by exposure to the environment.

The inner wall 260 is made in a preferred embodiment from a laminate including a linear low density film of 3 to 4 mils thickness, a high temperature adhesive layer, a clear foil layer, a second high temperature adhesive layer and a second linear low density film of 3 to 4 mils thickness, although other suitable materials may be used. The outer wall 262 is made in a preferred embodiment from a laminate including a linear low density film of 3 to 4 mils thickness, a high temperature adhesive layer, a clear foil layer, a second high temperature adhesive layer and an insulating layer, although other suitable materials may be used. The insulating layer may be made from any flexible insulating material well known to those skilled in the art and is used to retain the thermal energy generated within the first compartment 256. In one preferred embodiment, the insulating layer is a laminate including a 60 to 100 gauge biaxial oriented nylon sheet, a high temperature adhesive layer, a microfoam-blown polypropylene layer and a non-woven film, such as nylon.

The thermal packaging unit 250 also includes a top seal 268 that maintains a relatively moisture-free environment within the storage area 252. The top seal 268 is preferably resealable so as to allow the biocompatible implant 210 to be reinserted into the storage area 252. This may be necessary when the temperature of the biocompatible implant 210 cools to a temperature below its glass transition temperature before the insertion process can be attempted or successfully completed.

In this embodiment, the activation disk 280 is bent to initiate the reaction. Crystallization of the sodium acetate solution generates thermal energy within the first compartment 256 that is subsequently transferred from the first compartment 256 to the biocompatible implant 210, thereby causing the temperature of the biocompatible implant 210 to rise. The thermal packaging unit 250 can be reused for at least one additional use by boiling the thermal packaging unit 250 for a time sufficient to return the sodium acetate and water solution within the first compartment 256 to its previous state. Subsequent activation of the thermal packaging unit 250 is then accomplished in the same manner described above.

It will be noted that the first compartment 256 may contain a different chemical reactant which may be combined with a different suitable activating agent in the same manner described above to produce the desired exothermic or thermodynamic chemical reaction. It will also be noted that the first compartment 256 may be separated into segments by means of a separating wall, with a second activation disk added for making each half of thermal packaging unit 250 independently activated.

Figure 8:
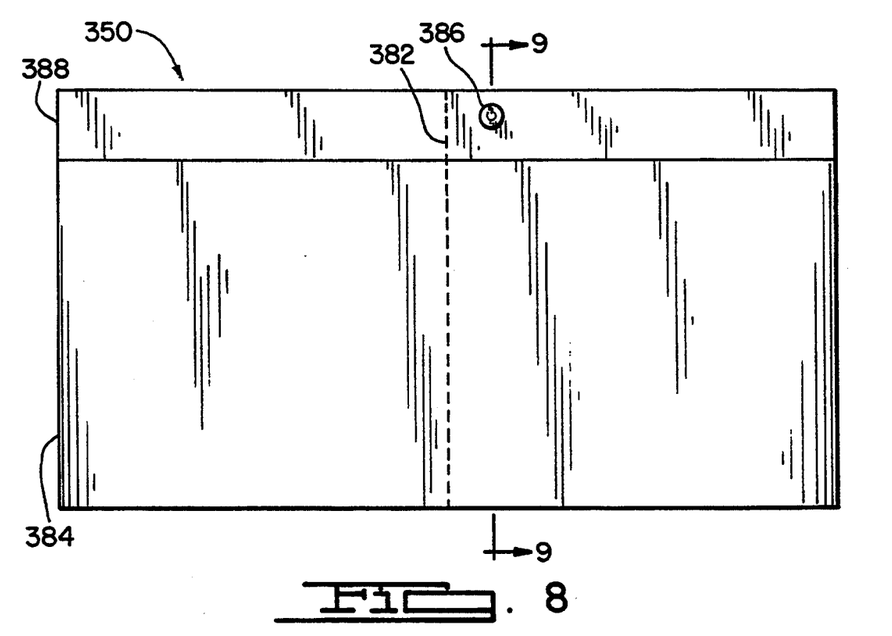
FIG. 8 is an elevational view of a thermal packaging unit used for heating the biocompatible implant shown in FIG. 2 according to the teaching of yet another preferred embodiment of the present invention.
Figure 9:
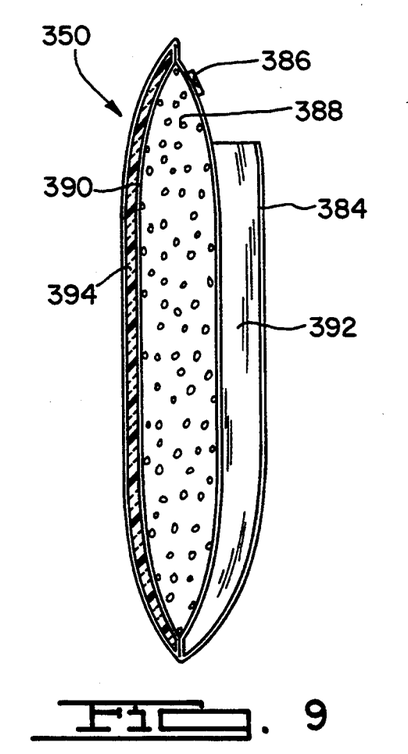
FIG. 9 is a cross-sectional view of the thermal packaging unit shown in FIG. 8.

A further embodiment of the thermal packaging unit, generally designated by the numeral 350, will now be described with reference to FIGS. 8 and 9. The thermal packaging unit 350 is shown to include a first compartment 388 defined by the outer wall 390, which is partially separated into two portions by a perforated seal 382 extending through the central portion of the first compartment 388.

Disposed near the center top portion of the thermal packaging unit 350 is an injection port 386 for introducing an activation compound for initiating an exothermic or thermodynamic chemical reaction. The injection port 386 is preferably mounted upon the external surface of the outer wall 390 thereby providing a resealable passageway through the outer wall 390 from the external surface of the thermal packaging unit 350 to the first compartment 388. The injection port 386 is made from a compliant material that can be deformed and penetrated from an initial relatively sealed condition to accept an injection instrument such as a syringe or other suitable tool (not shown). The injection port 386 preferably returns to a relatively sealed condition following the withdrawal of the injection instrument as before.

The thermal packaging unit 350 further includes a pocket 384 disposed on one side for defining a storage space 392 for holding a biocompatible implant (not shown) and enhancing heat transfer and retention. The thermal packaging unit 350 is initially in a flat orientation. After the biocompatible implant to be heated is located within the pocket 384, the thermal packaging unit 350 is folded about the perforated seal 382 to substantially surround the biocompatible implant. This arrangement promotes convenience in inserting the biocompatible implant into and removing it from the thermal packaging unit 350.

The thermal packaging unit 350 further includes an insulating layer 394 disposed upon the opposite surface of the thermal packaging unit 350 from the pocket 384. The insulating layer 394 may be made from any flexible insulating material well known to those skilled in the art and is used to retain the thermal energy generated within the first compartment 388 after the thermal packaging unit 350 is activated and is folded to surround the biocompatible bone plug being heated. In one preferred embodiment, as before, the insulating layer 394 is a laminate including a 60 to 100 gauge biaxial oriented nylon sheet, a high temperature adhesive layer, a microfoam-blown polypropylene layer and a non-woven film, such as nylon.

The first compartment 388 is operative to contain calcium chloride which is reacted with water introduced by an injection instrument through the injection port 386. As water combines with the calcium chloride in the first compartment 388, an exothermic or thermodynamic chemical reaction occurs whereby thermal energy is generated within the first compartment 386. When the thermal packaging unit 350 is in a folded condition, this generated heat is transferred from the first compartment 388 to the biocompatible implant stored within the pocket 384 which causes the temperature of the biocompatible implant to rise. It will be noted that the first compartment may contain a different chemical reactant which may be combined with water or a suitable activating solvent other than water in the same manner described above to produce the desired exothermic or thermodynamic chemical reaction.

The biocompatible implant can be removed from and reinserted into the pocket 384 as desired for satisfying the particular heating needs of an application. This may be necessary when the temperature of the biocompatible implant cools to a temperature below its glass transition temperature before the insertion process can be attempted or successfully completed. It should be noted that the folded condition of the thermal packaging unit 350 is more effective for developing a fully heated condition, as well as for maintaining a heated condition when a biocompatible implant is inserted into the pocket 384 and following removal of the implant, should a reheating become necessary.

While the above description discusses a preferred embodiment of the present invention, it will be understood that the description is exemplary in nature and is not intended to limit the scope of the invention. For example, the implant used in the present invention may be of a biocompatible or bioresorbable material. Also, the deformability characteristics of the implant may be altered by any change in thermochemical condition of the implant, such as exposure to one or more chemical compounds which react with the implant material so as to render it temporarily deformable prior to implantation. In addition, the thermal packaging unit may be supplied with an implant already positioned within the storage area or it may be supplied empty for insertion of an implant before activation. Furthermore, the thermal packaging unit may be used to enhance the sterility of the biocompatible implant from when the biocompatible implant is manufactured until immediately before the biocompatible implant is implanted. As will be appreciated by those skilled in the art, the use of the thermal packaging unit to enhance the sterility of the biocompatible implant reduces the costs which would otherwise be associated with enhancing the sterility of the biocompatible implant before implantation. In addition, the implant described herein may be used in connection with other types of surgical applications and with other types of tissue. Furthermore, other means such as a heated water bath, a stove or an iron may be used for heating the biocompatible implant. The present invention will therefore be understood as susceptible to modification, alteration and variation by those skilled in the art without deviating from the scope and meaning of the following claims.

What is claimed is:

1. A bone plug for use in partially defining an enclosed region within a cavity formed in living tissue, the living tissue being at a first temperature, said bone plug comprising:

a main body being operable to be inserted into the cavity;

a first flange protruding laterally from said main body for securing said main body within said cavity when said first flange is at a first thermochemical state defined at least in part by the first temperature, (a) said first flange being relatively nonelastic when said first flange is in said first thermochemical state so as to secure said bone plug within the cavity in the living tissue after said bone plug has been inserted into the cavity, (b) said first flange being relatively elastic at a second thermochemical state so as to allow said first flange to be deformable when said bone plug is forceably inserted into the cavity in the living tissue, said second thermochemical state being defined at least in part by a second temperature which is between the first temperature and about 70° C.; and said first flange being operable to return to said first thermochemical state from said second thermochemical state after said bone plug is inserted into the cavity in the living tissue.

2. The bone plug according to claim 1, further comprising a second of said flanges protruding laterally from said main body, said second flange being longitudinally spaced from said first of said flanges.

3. The bone plug according to claim 2, wherein said first and second flanges protrude laterally outwardly from said main body and have laterally-extending engagement surfaces thereon for at least partially engaging the living tissue when said bone plug is inserted into the cavity and the flanges are deformed, said engagement surfaces having a plurality of ridges disposed thereon for engaging the living tissue when said bone plug is inserted into the cavity and the 4. The bone plug according to claim 3, wherein said first and second flanges are formed from a material having a glass transition temperature above said normal temperature range of the living tissue.

5. The bone plug according to claim 4, wherein said at least first flange is formed from at least one polymer material selected from the group consisting of polyglycolide, polylactide, poly(glycolide-co-lactide), polydioxanone, poly(glycolide-co-trimethylene carbonate), poly(ethylene carbonate), poly(iminocarbonates), polycaprolactone, polyhydroxybutyrate, polyesters, poly(amino acids), poly(ester-amides), poly(orthoesters), poly(anhydrides) and cyanoacrylates and copolymers and blends thereof.

6. A bone plug for forming a barrier within a cavity formed in living tissue, the living tissue being at a first temperature, said bone plug comprising:

a main body being operable to be inserted into the cavity; and means for securing said main body in a substantially stationary position within the cavity, said means for securing said main body in a substantially stationary position (a) being relatively nonelastic when in a first thermochemical state so as to secure said bone plug within the cavity of the living tissue after said bone plug has been inserted into the cavity, said first thermochemical state defined at least in part by the first temperature, and (b) being relatively elastic at a second thermochemical state so as to be deformable when said bone plug is forceably inserted into the cavity in the living tissue, said second thermochemical state being at least partially defined by a temperature above the first temperature but less than about 70° C. where the living tissue suffers cell damage;

whereby said means for securing said main body in a substantially stationary position is operable to be converted from said first thermochemical state to said second thermochemical state prior to being inserted into the cavity, said means for securing said main body in a substantially stationary position is further operable to return to said first thermochemical state from said second thermochemical state after said bone plug is inserted into the cavity in the living tissue.

7. The bone plug according to claim 6, wherein said first thermochemical state is a said normal temperature range for the living tissue.

8. The bone plug according to claim 6, wherein said bone plug is bioresorbable.

9. The bone plug according to claim 6, wherein said means for securing said main body in a substantially stationary position within said cavity further comprises a flange disposed on said main body, said flange being deformable when said biocompatible implant is heated to said second temperature.

10. The bone plug according to claim 6, further comprising insertion means releasably said bone plug for inserting said bone plug into said cavity.

11. The bone plug according to claim 6, wherein said bone plug is formed from at least one polymer material selected from the group consisting of polyglycolide, polylactide, poly(glycolide-co-lactide), polydioxanone, poly(glycolide-co-trimethylene carbonate), poly(ethylene carbonate), poly(iminocarbonates), polycaprolactone, polyhydroxybutyrate, polyesters, poly(amino acids), poly(ester-amides), poly(orthoesters), poly(anhydrides), cyanoacrylates, and copolymers and blends thereof.

12. The bone plug according to claim 9, wherein said means for securing said main body in a substantially stationary position within said cavity further comprises a plurality of flanges disposed on said main body, each of said plurality of flanges being deformable when said biocompatible implant is heated to said second temperature.

13. The bone plug according to claim 9, wherein said flange has a first laterally-extending engagement surface with a plurality of ridges disposed thereon for at least partially engaging the living tissue when said bone plug is inserted into said cavity and said flange is deformed.

14. The bone plug according to claim 13, wherein said plurality of ridges are concentrically disposed on said engagement surface of said first flange.

15. A bone plug for use in partially defining an enclosed region within a cavity formed in living tissue, said living tissue being at a first temperature; said bone plug comprising:

a main body being operable to be inserted into the cavity;

a flange for securing said main body within said cavity when said flange is at said first thermochemical state, said first thermochemical state defined at least in pat by the first temperature, (a) said first flange being relatively nonelastic when said first flange is in the first thermochemical state so as to secure said bone plug within the cavity of the living tissue after said bone plug has been inserted into the cavity, (b) said first flange being relatively elastic at a second thermochemical state so as to allow said first flange to be deformable when said bone plug is forceably inserted into the cavity in the living tissue, said second thermochemical state being at least partially defined by a temperature above a normal temperature range for the living tissue but less than about 70° C.;

said flange protruding laterally outwardly from said main body and having a laterally-extending engagement surface thereon for at least partially engaging the living tissue when said bone plug is inserted into the cavity and said flange is deformed, said engagement surface having discontinuities thereon that protrude therefrom for engaging the living tissue when said bone plug is inserted into the cavity and the flange is deformed.

16. The bone plug according to claim 15, further comprising a second flange protruding from said main body, said second flange being longitudinally spaced from said first of said flanges.

17. The bone plug according to claim 16, wherein each of said first and second flanges has said discontinuities on said engagement surface thereof, said discontinuities including a plurality of ridges disposed thereon.

18. The bone plug according to claim 17, wherein said first and second flanges are formed from a material having a glass transition temperature above said normal temperature range of the living tissue.

19. The bone plug according to claim 18, wherein at least said first flange is formed from at least one polymer material selected from the group consisting of polyglycolide, polylactide, poly(glycolide-co-lactide), polydioxanone, poly(glycolide-cotrimethylene carbonate), poly(ethylene carbonate), poly(iminocarbonates), polycaprolactone, polyhydroxybutyrate, polyesters, poly(amino acids), poly(ester-amides), poly(orthoesters), poly(anhydrides) and cyanoacrylates and copolymers and blends thereof.

20. A bone plug for forming a barrier within a cavity formed in living tissue, said living tissue being at a first temperature, said bone plug comprising:

a main body being operable to be inserted into the cavity;

securing means for securing said main body to a substantially stationary position within the cavity, said securing means (a) being relatively nonelastic when in a first thermochemical state so as to secure said bone plug within the cavity of the living tissue after said bone plug has been inserted into the cavity, said first thermochemical state being defined at least in part by the first temperature, (b) being relatively elastic at a second thermochemical state so as to be deformable when said bone plug is forceably inserted into the cavity in the living tissue, said second thermochemical state being defined at least in part by a second temperature which is between the first temperature and about 70° C.; and said securing means further includes a laterally-extending engagement surface located thereon, said engagement surface including discontinuities thereon for at least partially engaging the living tissue when said bone plug is inserted into said cavity and said securing means is deformed by said engagement with the living tissue, whereby said securing means is operable to be converted from said first thermochemical state to said second thermochemical state prior to be inserted into said cavity, said means for securing is further operable to return to said first thermochemical state from said second thermochemical state after said bone plug is inserted into the cavity in the living tissue.

21. The bone plug according to claim 20, wherein said bone plug is bioresorbable.

22. The bone plug according to claim 20, wherein said securing means further comprises a laterally-extending flange disposed on said main body; said flange having said engagement surface thereon being deformable when said biocompatible implant is heated to said second temperature.

23. The bone plug according to claim 22, wherein said securing means further comprises a second laterally-extending flange disposed on said main body, said second flange also being deformable when said biocompatible implant is heated to said second temperature.

24. The bone plug according to claim 22, wherein said discontinuities include a plurality of ridges disposed on said engagement surface.

25. The bone plug according to claim 24, wherein said plurality of ridges are concentrically disposed on said engagement surface of said flange.

26. The bone plug according to claim 20, further comprising insertion means releasably engageable with said bone plug for inserting said bone plug into said cavity.

27. The bone plug according to claim 20, wherein said bone plug is formed from at least one polymer material selected from the group consisting of polyglycolide, polylactide, poly(glycolide-co-lactide), polydioxanone, poly(glycolide-co-trimethylene carbonate), poly(ethylene carbonate), poly(iminocarbonates), polycaprolactone, polyhydroxybutyrate, polyesters, poly(amino acids), poly(ester-amides), poly(orthoesters), poly(anhydrides), cyanoacrylates and copolymers and blends thereof.

* * * * *

UNITED STATES PATENT AND TRADEMARK OFFICE
CERTIFICATE OF CORRECTION

PATENT NO. : 5,376,120
DATED : December 27, 1994
INVENTOR(S) : Sarver, et al

It is certified that error appears in the above-identified patent and that said Letters Patent is hereby corrected as shown below:

Column 2, line 25, "pollution" should be --portion--.

Column 3, line 27, "," should be --.--.

Column 3, line 47, "." should be --;--.

Column 12, line 62, claim 3, after "the" (second occurence in patent) insert --flanges are deformed--.

Column 13, line 53, claim 10, after "releasably" insert --engageable with--.

Column 14, line 14, claim 15, ";" should be --,--.

Column 14, line 21, claim 15, "pat" should be --part--.

Column 14, line 60, claim 19, "poly(glycolide-cotrimethylene" should be --poly(glycolide-co-trimethylene--.

Column 15, line 29, claim 20, "be" should be --being--.

Signed and Sealed this

Sixteenth Day of June, 1998

Attest:

BRUCE LEHMAN

*Attesting Officer*   *Commissioner of Patents and Trademarks*